United States Patent
Sneyders

(10) Patent No.: US 9,903,706 B2
(45) Date of Patent: Feb. 27, 2018

(54) CRIMPING MEASURING DEVICE

(71) Applicant: Exmore Benelux BVBA, Beerse (BE)

(72) Inventor: Luc Sneyders, Beerse (BE)

(73) Assignee: Exmore Benelux BVBA, Beerse (BE)

( * ) Notice: Subject to any disclaimer, the term of this patent is extended or adjusted under 35 U.S.C. 154(b) by 0 days.

(21) Appl. No.: 15/513,721

(22) PCT Filed: Aug. 31, 2016

(86) PCT No.: PCT/IB2016/055190
§ 371 (c)(1),
(2) Date: Mar. 23, 2017

(87) PCT Pub. No.: WO2017/093815
PCT Pub. Date: Jun. 8, 2017

(65) Prior Publication Data
US 2017/0307356 A1      Oct. 26, 2017

(30) Foreign Application Priority Data

Dec. 2, 2015   (BE) .................................. 2015/5778

(51) Int. Cl.
*G01N 21/00*    (2006.01)
*G01B 11/02*    (2006.01)
(Continued)

(52) U.S. Cl.
CPC .......... *G01B 11/02* (2013.01); *H01R 43/0488* (2013.01); *G01J 3/02* (2013.01); *G01N 21/64* (2013.01); *G03F 7/70625* (2013.01)

(58) Field of Classification Search
CPC .......... G01B 11/02; G01B 11/14; G01B 11/24; H01R 43/0488; H01J 37/32935;
(Continued)

(56) References Cited

U.S. PATENT DOCUMENTS

| 5,421,101 A | 6/1995 | Rank |
| 2012/0263344 A1 | 10/2012 | Viviroli |
| 2015/0155673 A1* | 6/2015 | Kawamura ............ H01R 43/02 29/860 |

FOREIGN PATENT DOCUMENTS

| EP | 964485 A1 | 12/1999 |
| EP | 1780846 A1 | 5/2007 |

OTHER PUBLICATIONS

International Search Report and Written Opinion, completed Oct. 24, 2017, pertaining to PCT/IB2016/055190, filed Aug. 31, 2016.
(Continued)

*Primary Examiner* — Abdullahi Nur
(74) *Attorney, Agent, or Firm* — Dinsmore & Shohl LLP

(57) ABSTRACT

The present invention relates to a measuring device for determining the height of a crimp in a crimp connector to a conductor, such as in a cable lug or ferrule. The Exmore CRIMPING MEASURING DEVICE is a crimp height and crimp width measuring system, developed for highly precise measuring of crimp contacts.

The invention is characterized by changes in the blade as used in a micro-metric measuring device. The measuring device according to the invention comprises a measuring knife comprising a resilient tool, further comprising a plate-shaped tool which is placed centrally in the measuring knife and which is placed perpendicularly to the orientation of the measuring knife. Measurement is performed manually and independent of any operator-related influences by way of centering unit. The Exmore CRIMPING MEASURING DEVICE simplifies the crimp height measurement process resulting in faster measurement time and improved consistency, acquired measured values can be read off, transferred via the serial interface or optionally printed.

18 Claims, 5 Drawing Sheets

(51) Int. Cl.
*H01R 43/048* (2006.01)
*G01N 21/64* (2006.01)
*G01J 3/02* (2006.01)
*G03F 7/20* (2006.01)

(58) Field of Classification Search
CPC ........ G01N 21/64; G01N 21/68; G01N 21/47;
G01N 2015/1037; G01J 3/02
See application file for complete search history.

(56) References Cited

OTHER PUBLICATIONS

Belgium Search Report, completed Mar. 17, 2016, pertaining to BE2015/5778, filed Dec. 2, 2015.

\* cited by examiner

CRIMPING MEASURING DEVICE

FIELD OF THE INVENTION

The present invention relates to a measuring device for determining the height of a crimp in a crimp connector/contact on a conductor, such as in a cable lug or ferrule. The Exmore CRIMPING MEASURING DEVICE is a crimp height and crimp width measuring system, developed for highly precise measuring of crimp contacts. Measurement is performed manually and independent of any operator-related influences by way of centering unit. The Exmore CRIMPING MEASURING DEVICE simplifies the crimp height measurement process resulting in faster measurement time and improved consistency, acquired measured values can be read off, transferred via the serial interface or optionally printed.

BACKGROUND TO THE INVENTION

Automatic crimping presses have been used for a long time in the connector industry to run high-speed crimps of various ropes and harnesses, for example in the field of electronics, telecommunications and automotive electronics. In the crimping process an electrical and mechanical connection is achieved by pressing together the conductor in a crimp sleeve. The crimp height of the crimped contact is a key criterion to assess the quality of the formed crimp connection. Connections that do not meet the prescribed crimp height cannot be further processed.

Today the crimp heights are often measured manually, either directly on the wire-crimping machine or on a separate measuring location, for example, by making use of a micrometer or with a measuring device which is equipped with a digital gauge. Regardless of the method used, the crimp height can only be determined accurately by proper placement and orientation of the crimp in the measuring device. An incorrect placement and/or orientation gives rise to undesirable errors, this is not a problem in itself were it not that these errors cannot be recognized by the user as such (as a result of an erroneous manipulation).

So it should come as no surprise that today there has already been sought for solutions in order to meet the above-mentioned problems in determining the crimp height of a crimp connection. In a first approach, as described for example in EP 1780846, the measuring device is provided with mechanical tools which grab the crimp connection to be measured and provide a correct orientation and positioning of the crimp connection between the measuring head. In EP 1780846 the upper side of the measuring head comprises arms which are closed on the crimp connection, and thus ensure the horizontal orientation. In order to ensure that the crimp is centrally positioned between the measuring head, the underside of the measuring head is provided with a centering which only permits a measurement upon contact with the said arms. In a different approach, as described in US 2012/0263344, one will optically follow the placing of the crimp in the measuring apparatus, and give feed-back to the user. The optical measurement will also be able to correct limited errors in orientation and placement. The disadvantage of such optical methods is the absence of a tactile feedback to the user. In the first approach, the measuring device completely takes over the correct placement from the user. The latter is particularly useful in the light of the miniaturization wherein the compounds to be manipulated are becoming smaller and where there is a need for a maximum automatization.

Nevertheless there is still a need for simple measuring devices that address these problems. Therefore the present invention has the goal to provide a simple measuring device to determine the crimp height of a crimp in a reproducible manner.

SUMMARY OF THE INVENTION

The determination of the crimp height is a quality determining parameter during a crimping process. Regardless of the method used, the crimp height can only be determined accurately by proper placement and orientation of the crimp in the measuring device. After all, an incorrect placement and/or orientation gives rise to undesirable measurement errors. To avoid this problem, we provide a measuring device which is characterized by changes in the knife-edge as used in a micro-metric measuring device. The measuring device based on the invention differs from other measuring devices in the fact that the measuring knife is provided with a resiliently erected tool, whereby this tool consists of a plate-shaped tool which is centrally placed in the measuring knife and which is perpendicular to the orientation of the measuring knife. This adaptation of the measuring knife allows to accurately determine the most important quality parameter (i.e. the crimp height).

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

As already mentioned herein, the goal of the present invention is to offer a measuring device for determining the crimp height of a crimp in a reproducible manner. Therefore the invention is characterized by changes in the blade as used in a micro-metric measuring device.

Figure 1:
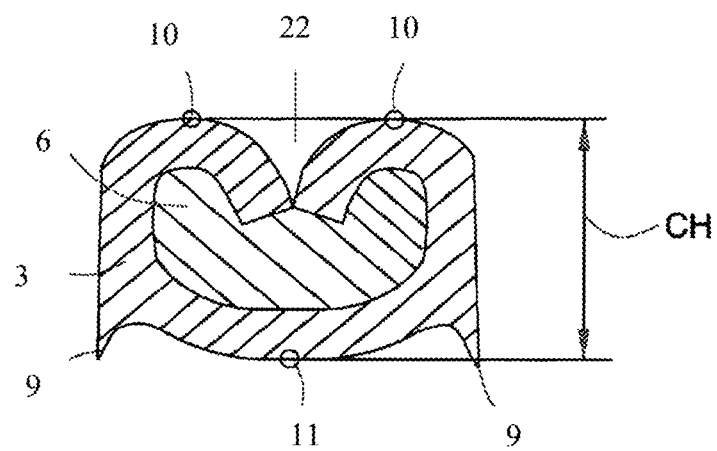
FIG. 1: Is a cross-sectional view of a crimp connector (3) with the central conductor (6) of the cable which is placed in the cable connector. The cross section shows the profile which was formed during the crimping, with the formation of a groove at the upper side (22) and a pair of crimp edges (9) at the bottom. The crimp height CH is also indicated.
Figure 2:
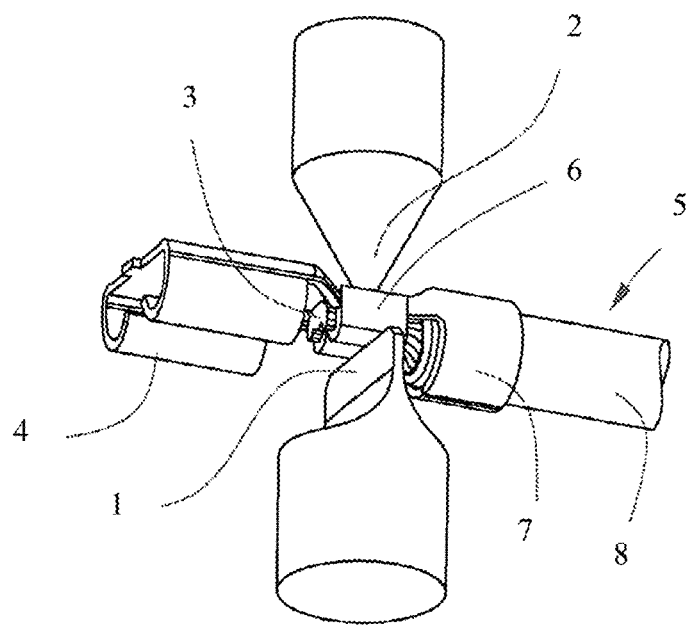
FIG. 2: Is a perspective drawing of a measuring device according to the state of the art. This image shows an electrically insulated cable (5) with a crimp with a cable lug (4) at the free cable end. The insulated cable end (8) is connected to the cable lug with an insulation crimp (7) and the conductor end (6) is pressed into the crimp connector (3). The height of the crimp is determined by placing the crimp connector perpendicularly and centrally between a measuring knife (1) and measuring point (2).

As shown in the cross-section in FIG. 1, a profile will be pressed when crimping the crimp press by means of a crimp punch in the crimp connector (3) of the cable lug for example. Typically a groove (22) is formed at one side, hereinafter also referred to as the conductor groove. On the opposite side, crimping edges (9) are typically formed which are the result of the necessary clearance between the crimp punch and the anvil. By reference to FIG. 2, the height a crimping (CH) will then be measured by placing the side with the groove, hereafter called the groove side, on a measuring knife (1) and letting a measuring point (2) rest on the crimp connector at the opposite side, hereinafter also referred to as the base of the crimp connector. The crimp height then corresponds to the distance between the contact points on the groove side (10) and contact point on the base (11) as shown in FIG. 1.

Figure 3:
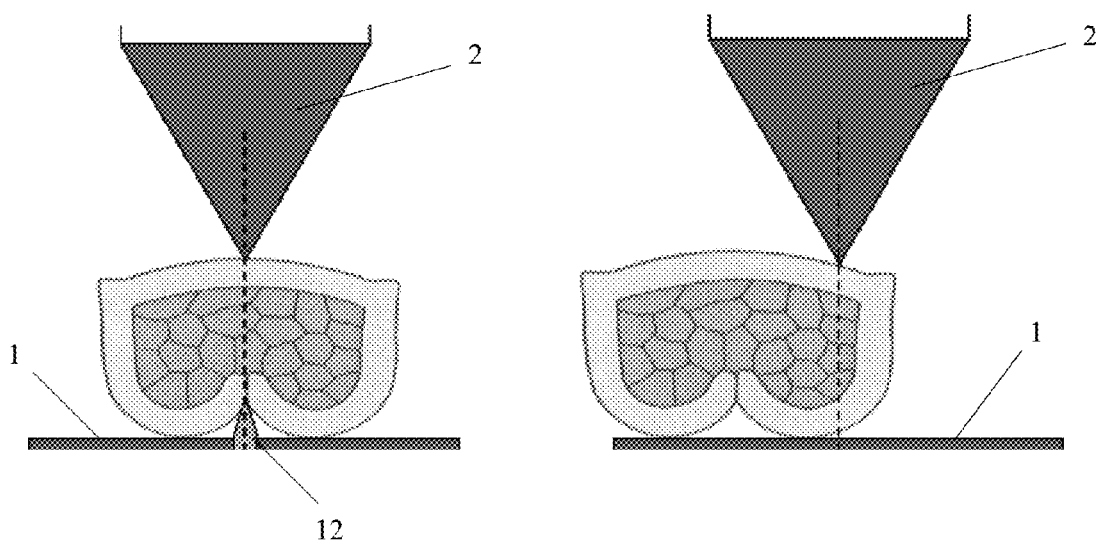
FIG. 3: Shows in cross section the difference between a measuring device according to the state of the art (B) and the measuring device according to the present invention (A). The tool (12) fits in the groove of the crimp connector and thus ensures a correct positioning.
Figure 6:
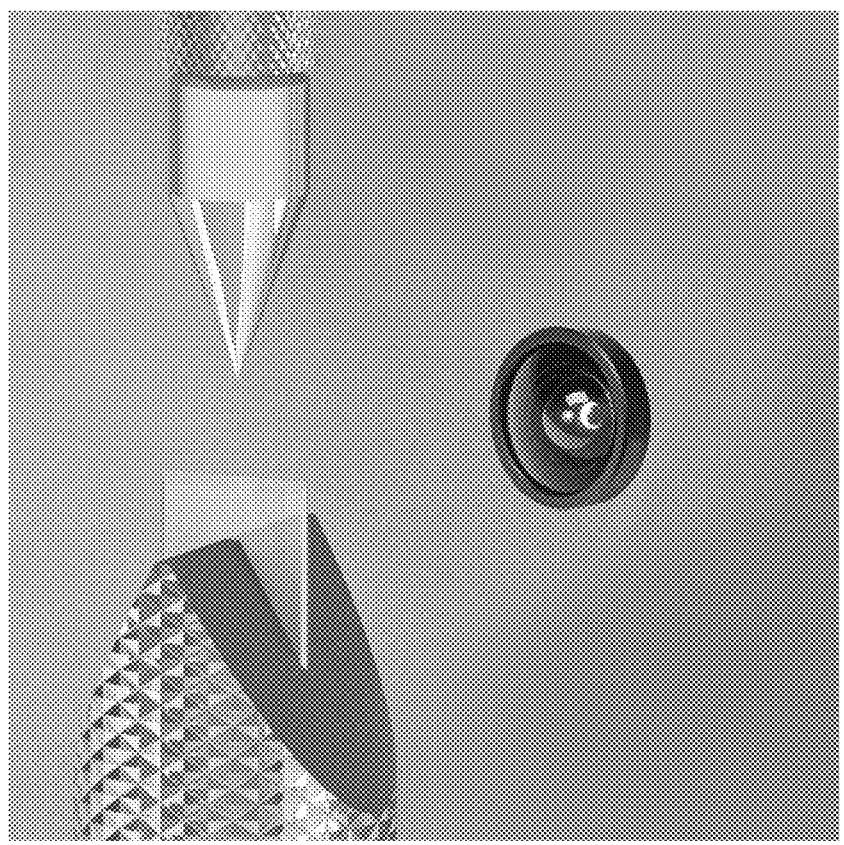
FIG. 6: Shows the position of the camera that can make images of the measured crimp contact and which then can be stored. The camera is a CCD-type camera with optical lens.

A correct positioning of the crimp between the knife and the measuring point is essential in order to obtain a good measurement. As shown in FIG. 3 an eccentric placement will give rise to measurement errors. In order to prevent this, the measuring knife of the measuring device is provided with a resiliently erected tool (12) (a plate-shaped element) for the correct positioning of the crimp to be measured. The plate-like tool is centrally and perpendicular placed to the orientation of the measuring knife. Upon placement of the crimp to be measured, the tool ends up in the conductor groove and thus not only provide correct centering of the crimp, but also assists in the placement at the correct angle, in particular orthogonal, relative to the measuring knife. In a particular embodiment, the measuring device is provided with a camera, preferably a CCD-type camera with optical lens. In this embodiment, the lens of the camera is perpendicular placed relative to the crimping knife and at the same height relative to the crimp contact as shown in FIG. 6, by which images of the measured contact can be made.

Figure 7:
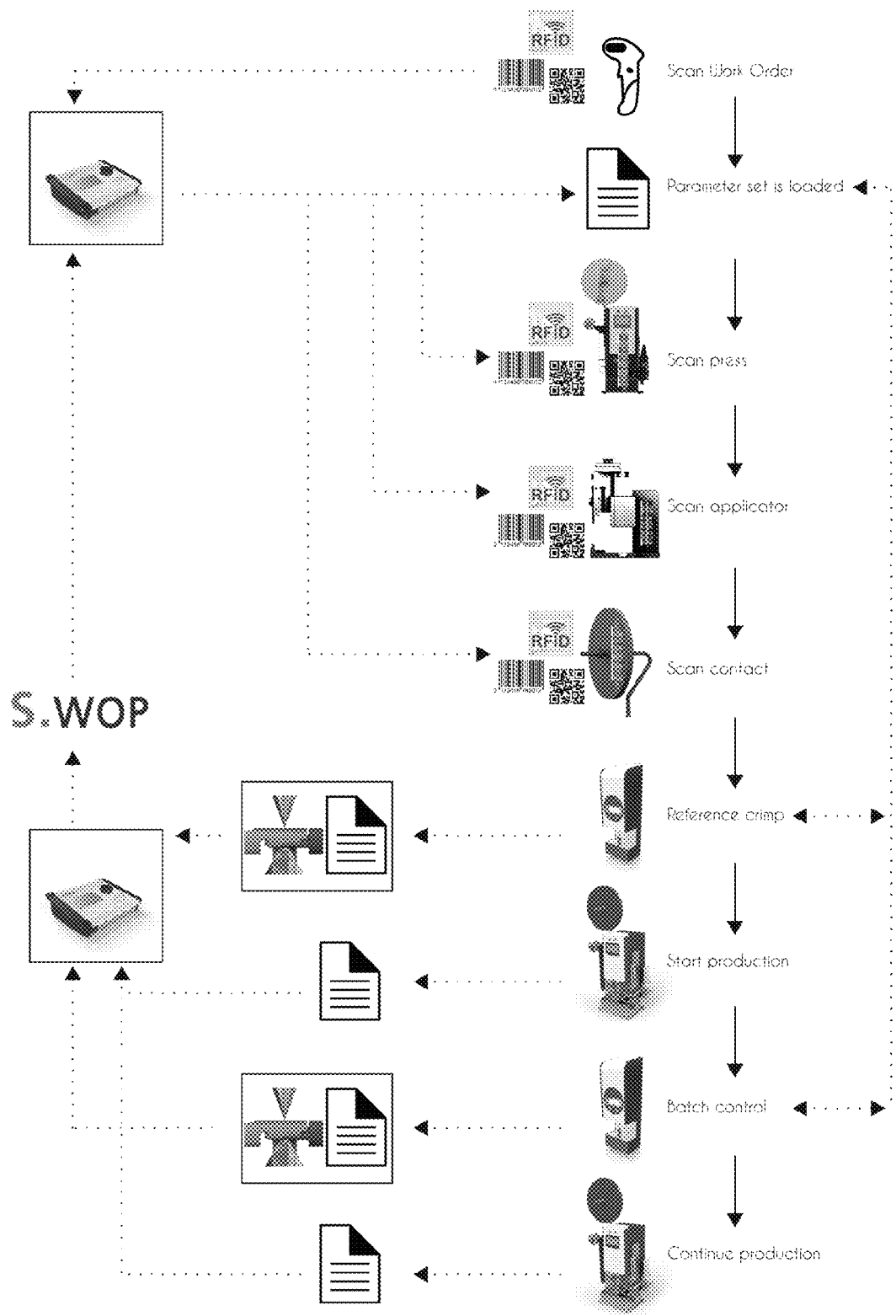
FIG. 7: shows the operation of the traceability software. After setting the parameters for the crimping device, the process can be started with the scanning of a barcode, a QR code or via RFID. First of all, a reference crimp is performed. If this turns out positive, the production can be started, and a continuous production can be maintained through batch controls (batch size to be determined by the user). If the reference crimp or batch control is negative, then the parameters must be adjusted and the process will be repeated with new parameters.

The measuring device according to the invention can also be provided with traceability software in which the production is started by logging a code for a work order, for example, by scanning a bar code, QR-code, or RFID, this allows to follow up errors and parameter adjustments in the crimping process. As far as the crimping device is also provided with a camera, the recorded images from the CCD camera can be linked with the code of a given work order. A schematic representation of this process is shown in FIG. 7.

In order to determine the zero set, which is the contact height between the measuring point and knife, the knife is placed in a holder (17) which allows a lateral displacement of the knife, and therefore allows the measurement point next to the tool on the measuring knife to make contact to set the zero point. In a specific embodiment, the container is cylindrical in which the knife is eccentrically placed. In another embodiment, there is the integration of softclosure which provides an automatic closure of the measuring device when a connection is held in it.

Figure 4:
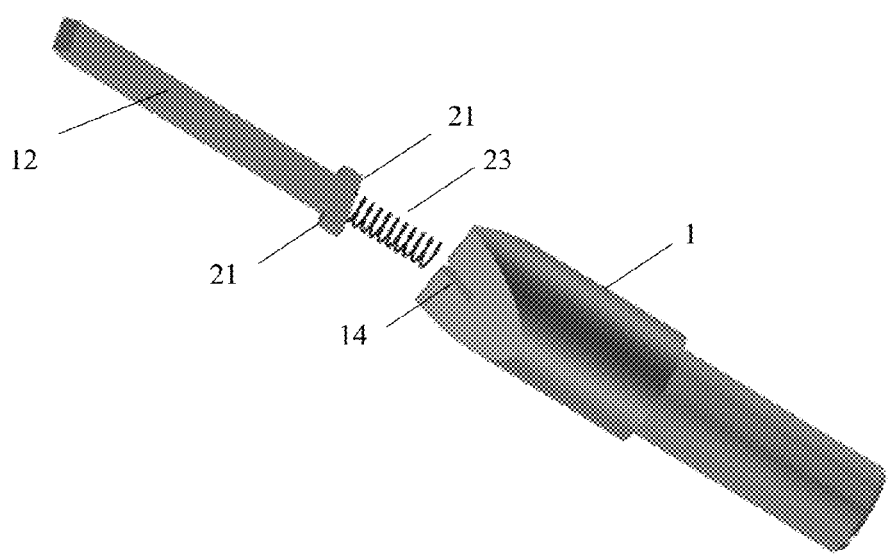
FIG. 4: Is a perspective view of the structure of a measuring knife (1) according to the present invention. It shows the perpendicular and central presence of a groove (14) into which a plate-shaped tool (12) fits. Cams (21) at the bottom prevent that the tool will be pushed out completely of the measuring knife by the spring (23).
Figure 5:
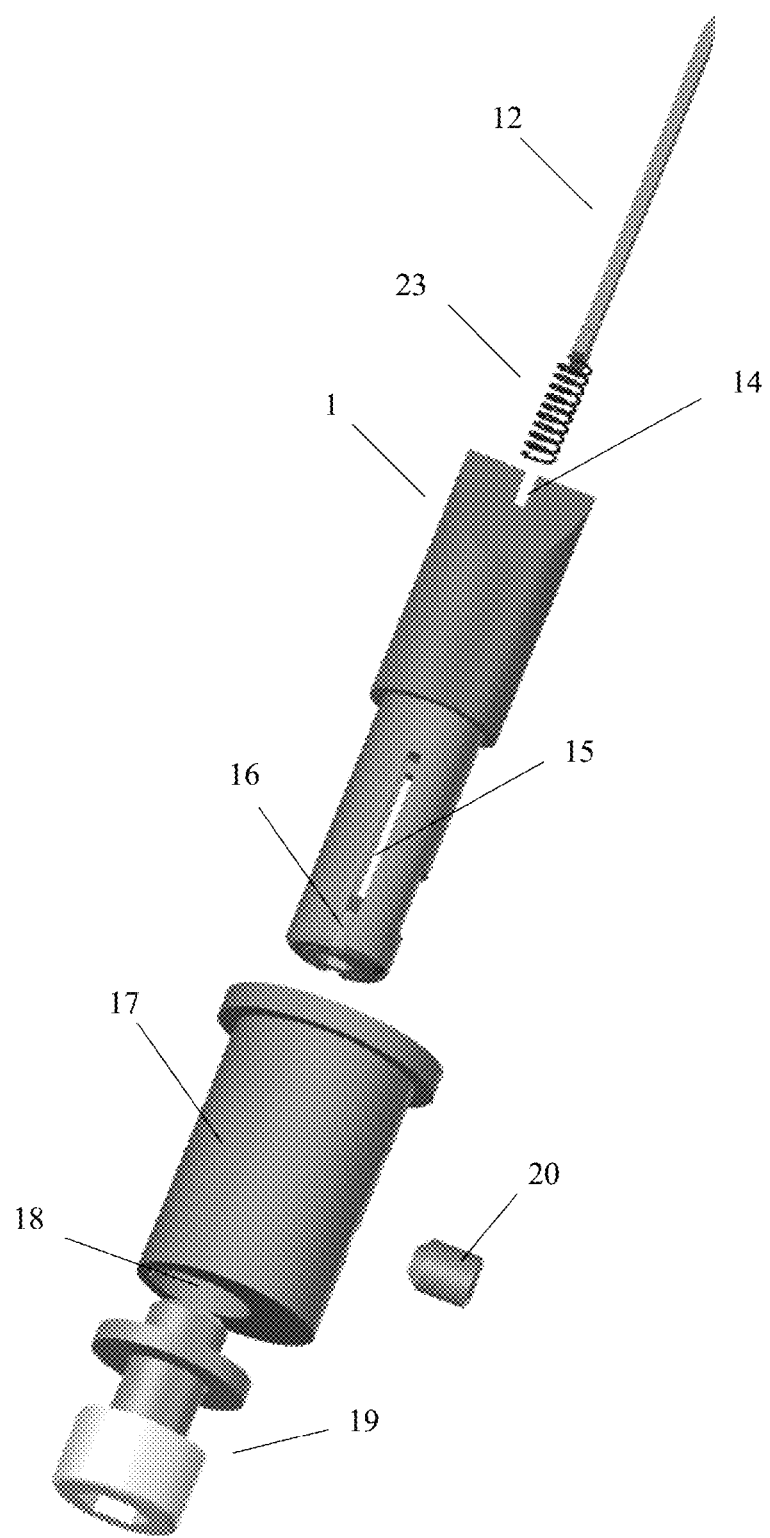
FIG. 5: Is a perspective view of the structure of a measuring knife (1) according to the present invention and the associated holder (17). This image shows a cavity (15) in the knife in front of the tool (12) and spring (23), with a removable bottom (16). This section fits in an eccentric recess (18) in the cylindrical holder (17), wherein the knife in fixed in the holder with blocking means (20).

As shown in FIG. 4, the knife is provided with a groove (14) into which the tool (12) and resilient element (13) fit. In FIG. 5 we also see a removable bottom (16) which allows it to insert the tool and resilient element (13) in the measuring knife (1). This removable bottom also serves as a drop off point at the inner side for the resilience of the resilient element so that the latter is pushed to the outside. Cams (21) at the base of the device ensure that the device is not entirely pushed out of the measuring knife.

In a specific embodiment, the resilient element consists of a spring (23). This spring (23) located in a furnished cavity (15) in the measuring knife, pushes the device up against the cam(s) in the measuring knife. The tool (12) is plate-shaped and fits into a corresponding groove (14) in the measuring knife. In a specific embodiment, the plate-shaped tool can be compared to the blade of a sword, which has a sharp edge at the top. Thus, in a preferred form of the present invention, the upper side of the plate-shaped tool ends into a sharp edge (i.e., thinner at the top). The shape on the upper side of the plate-shaped tool can be any conventional shape that ends in a central thinner part, such as the sharpening angles Scandi, High flat, Full Flat, High Convex or Full Convex such as used in the blade of a knife. The ending in a sharp edge ensures that the plate-shaped tool deeply fits in the conductor groove which is beneficial for the positioning. The groove in the measuring knife is positioned centrally and opposite if the container is in the measuring position. In the illustrated embodiment, the holder (17) can be rotated by means of bolt (19) at the bottom. In the illustrated embodiment, the holder for the measuring knife is cylindrical and an eccentric recess (18) ensures that a lateral displacement of the measuring knife relative to the measurement point can be realized by simply turning the holder.

Together with the further details of the holder and the measuring knife this description illustrates the inventions, as defined in the following claims.

The invention claimed is:

1. A measuring device for measuring the crimp height (CH) of a crimp in a crimp connector, comprising a measuring knife provided with a resilient tool, whereby this tool consists of a plate-shaped tool which is centrally placed in the measuring knife and which is perpendicular to the orientation of the measuring knife.

2. The measuring device according to claim 1, wherein the crimping device also includes a holder for the measuring knife.

3. The measuring device according to claim 2, wherein the measuring knife by means of the holder is laterally movable opposite to measurement point.

4. The measuring device according to claim 2, wherein the holder is cylindrical.

5. The measuring device according to claim 4, wherein the measuring knife is eccentrically placed into the holder.

6. The measuring device according to claim 2, wherein the holder includes an engagement point in order to laterally displace the holder.

7. The measuring device according to claim 1, wherein the measuring knife is provided with a groove for the tool.

8. The measuring device according to claim 1, wherein the measuring knife is provided with a cavity for a resilient element.

9. The measuring device according to claim 1, wherein the measuring knife is provided with a removable bottom.

10. The measuring device according to claim 1, wherein it is provided with a softclosure that provides for an automatic closure of the measuring device when a contact is held in it.

11. The measuring device according to claim 1, wherein the plate-shaped tool ends in a sharp point at the top.

12. The measuring device according to claim 1, wherein the plate-shaped tool on the bottom side is provided with one or more cams.

13. The measuring device according to claim 1, wherein the measuring device is provided with a camera.

14. The measuring device according to claim 13, wherein the camera is positioned perpendicularly to the measuring knife and at the same height as the crimp contact.

15. The measuring device according to claim 1, wherein the measuring device is provided with traceability software, which ensures to monitor the crimping process and to adjust crimp parameters flexibly during production.

16. The measuring device according to claim 6, wherein the engagement point is a bolt for rotating the holder.

17. The measuring device according to claim 8, wherein the resilient element is a spring.

18. The measuring device according to claim 13, wherein the camera is a CCD type camera with optical lens.

* * * * *